US006939563B2

(12) United States Patent
Corpet et al.

(10) Patent No.: US 6,939,563 B2
(45) Date of Patent: Sep. 6, 2005

(54) NON-FERMENTED OSMOTIC LAXATIVE AND METHOD FOR TREATING AND PREVENTING COLORECTAL CANCERS

(75) Inventors: Denis Corpet, Toulouse (FR); Sylviane Tache, Leguevin (FR); Géraldine Parnaud, Baixas (FR)

(73) Assignees: Inra-Institut National de la Recherche Agronomique (FR); ENVT-Ecole Nationale Veterinaire de Toulouse (FR)

( * ) Notice: Subject to any disclaimer, the term of this patent is extended or adjusted under 35 U.S.C. 154(b) by 286 days.

(21) Appl. No.: 09/836,971

(22) Filed: Apr. 18, 2001

(65) Prior Publication Data

US 2001/0051659 A1 Dec. 13, 2001

Related U.S. Application Data

(63) Continuation of application No. PCT/FR99/01065, filed on May 5, 1999.

(30) Foreign Application Priority Data

Oct. 27, 1998 (FR) .............................................. 98 13450
Mar. 16, 1999 (FR) .............................................. 99 03240

(51) Int. Cl.$^7$ ............................... A61K 9/14; A61K 9/00

(52) U.S. Cl. ........................ 424/489; 424/400; 424/436; 424/78.08; 424/78.19; 514/892

(58) Field of Search .................................. 424/400, 489, 424/432, 436, 78.08, 78.19; 514/892

(56) References Cited

FOREIGN PATENT DOCUMENTS

EP       0 444 625 A1    9/1991

OTHER PUBLICATIONS

M.C. Crowson et al., *The Use and Efficacy of Cytocidal Agents in Colorectal Cancer,* Surg. Res. Com. 1987, vol. 2, pp. 97–101.

J. Hosoda et al., *Antitumor Activity of Doxorubicin Encapsulated in Poly(Ethylene Glycol)–Coated Liposomes,* Biol. Pharm. Bull. Sep. 1995, vol. 18, No. 9, pp. 1234–1237.

Primary Examiner—James M. Spear
Assistant Examiner—Lakshmi Channavajjala
(74) Attorney, Agent, or Firm—DLA Piper Rudnick Gray Cary US LLP

(57) ABSTRACT

Use of a non-fermented osmotic laxative as an active agent for preparation of a medicinal product for treating and/or preventing colon and/or rectum cancers. A method of treating or preventing colon or rectum cancer comprising administering to a mammal a therapeutically effective amount of a non-fermented osmotic laxative.

12 Claims, No Drawings

NON-FERMENTED OSMOTIC LAXATIVE AND METHOD FOR TREATING AND PREVENTING COLORECTAL CANCERS

RELATED APPLICATION

This is a continuation of International Application No. PCT/FR99/01065, with an international filing date of May 5, 1999, which is based on French Patent Application No. 98/13450, filed Oct. 27, 1998, and French Patent Application No. 99/03240, filed Mar. 16, 1999.

FIELD OF THE INVENTION

This invention concerns the prevention and treatment of adenomas and cancers of the colon and rectum. These tumors, in non-smokers, are the leading cause of cancer deaths.

BACKGROUND

The treatments currently available are based on surgical excision of the tumors, with adjunct chemotherapy, using 5-Fluorouracil, for example. These treatments have numerous drawbacks among which particular mention may be made of the high failure rate (40% survival rate after five years), the high cost for public funds and considerable patient suffering.

It has also been considered to prevent digestive cancers through the chronic administration of aspirin or an equivalent NSAID. However, this type of treatment leads to further considerable side effects and remains relatively ineffective.

Accordingly, it would be highly advantageous to provide new, easy-to-use means to prevent and/or effectively cure adenomas and cancers of the colon and rectum.

SUMMARY OF THE INVENTION

This invention relates to use of a non-fermented osmotic laxative as an active agent for preparation of a medicinal product for treating and/or preventing colon and/or rectum cancers.

This invention also relates to a method of treating colon or rectum cancer including administering to a mammal a therapeutically effective amount of a non-fermented osmotic laxative and a method of preventing colon or rectum cancer including administering to a mammal a therapeutically effective amount of a non-fermented osmotic laxative.

DETAILED DESCRIPTION

This invention includes the use of a non-fermented osmotic laxative as active agent in the preparation of a medicinal product intended to treat and/or prevent cancers of the colon and/or rectum. Preferably, the non-fermented osmotic laxatives which come within the scope of this invention are polyols.

By "laxative," we mean any compound having laxative and/or gelling properties. These are compounds able to attract and retain water inside the colon due to their physical-chemical properties, and to increase fecal excretion without fibers. Indeed, it is known that the consumption of fibers increases the mass and hydration of feces. Fibers, however, are fermented by intestinal microflora into volatile fatty acids which partake in the laxative effect of the fibers. One of the volatile fatty acids, butyrate, is thought to be involved in the protective effect of fibers against colorectal cancers. However, it has been observed that butyrate normalizes the growth of tumoral cells in vitro, and in vivo butyrate might increase apoptosis and, hence, the suicide of tumorous cells. Three major types of fibers have been studied for their preventive effect against cancer of the colon:

insoluble fibers, such as wheat bran and cellulose, soluble fibers such as oat bran, psyllium or ispaghula (Alabaster O., Tang Z. C., Frost A. and Shivapurkar N. (1993) Potential synergism between wheat bran and psyllium-enhanced inhibition of colon cancer. Cancer Letters. 75: 53–58), indigestible sugars such as inulin or lactulose (Challa A., Rao D. R., Chawan C. B. and Shackelford L. (1997) Bifidobacterium longum and lactulose suppress azoxymethane-induced colonic aberrant crypt foci in rats, Carcinogenesis, 18: 517–521; Reddy B. S., Hamid R. and Rao C. V. (1997) Effect of dietary oligofructose and inulin on colonic preneoplastic aberrant crypt foci inhibition, Carcinogenesis 18: 1371–1374; Roncucci L., DiDonato P. and PonzDeLeon M. (1993) Antioxidant vitamins or lactulose for the prevention of the recurrence of colorectal adenomas, Dis Colon Rectum, 36: 227–234; Rowland I. R., Rumney C. J., Coutts J. T. and Lievense L. C. (1998) Effect of bifidobacterium longum and inulin on gut bacterial metabolism and carcinogen-induced aberrant crypt foci in rats, Carcinogenesis, 19: 281–285).

These three types of fibers, to which digestion-resistant starch may be added, have protective properties against cancer.

Non-fermented, osmotic laxatives, that are the subject of this invention, such as PEGs, are not fibers since:

they are not of polyose chemical type (chain of simple sugars), they are not fermented by intestinal microflora and do not yield butyrate, they are not derived from plant walls.

In a remarkable manner, these non-fermented, osmotic laxatives that are the subject of this invention, such as PEG, have an anti-cancer effect which is not connected with butyrate and which is much more powerful than that of fibers, and their laxative property is probably due to their osmotic effect.

Among the non-fermented osmotic laxatives, the invention more particularly concerns the use of polyethylene glycol or polyethylenepolypropylene glycol, or a mixture or derivative thereof.

Polyethylene glycol (PEG) is a well-known polymer, used in particular as an additive in pharmaceutical compositions, having the following formula (I):

$$H-(O-CH_2-CH_2)_n-OH \qquad (I)$$

in which n is in the order of about 200 for high molecular weight PEGs, for example, PEG 8000.

High molecular weight PEGs, that is to say higher than approximately 3000, are known for their laxative effects. It is considered that PEGs attract and withhold water in the intestine via an osmotic effect (Davis G. R., SantaAna C. A. et al., 1980, Gastroenterology, 79: 35–39). Hence, PEG is used in humans in various preparations either as a preparatory wash before colonoscopy (4 liters, 236 to 360 g PEG), or as a laxative (3 to 40 g/day). As examples of such preparations the following may be cited:

Transipeg which is a macrogol-based iso-osmotic laxative (PEG with a molecular weight of 3350), presented in sachets containing 2.95 g PEG and an excipient made up of NaCl, anhydrous $Na_2SO_4$, $Na_2CO_3$, apple flavoring, aspartame. Macrogol is a polymer on which water molecules are withheld by hydrogen bonds. The PEG is apparently neither resorbed nor does it undergo bio-conversion and remains confined within the intestine (Vidal 1996, p. 1625).

Forlax 10 g presented in powder form for a drinkable solution containing macrogol 4000 and an excipient made of sodic saccharine, orange-grapefruit flavoring (Vidal 1996, p. 649).

Colyte and Golytaly which is marketed in the USA and contains PEG with a molecular weight of 3350. Colyte was recently proposed to promote the survival of CFTR mice in a cystic fibrosis model (Clarke L. L., Gawenis L. R., Franklin C. L., Harline M. C., 1966, Lab. Anim. Sci. 46: 612–618).

The efficiency of 20 g PEG 4000, with neither excipient nor electrolytes, in fighting against chronic constipation has also been demonstrated in a recent double-blind randomized trial (Hudziak H., Bronowicki J. P. et al., 1996, Gastoenterol. Clin. Biol. 20: 418–423).

Moreover, a test conducted on colon cancer cells HT29 did not show any significant cytocide effect of PEG compared with the control solution (Crowson et al., 1987, Surgical Res. Com. 2: 97–101).

We have been able to identify the unexpected capability of PEG and its derivatives to prevent or cure colorectal cancers. In its use as an additive, PEG is known to be used as a vehicle for various molecules, in particular anti-cancer chemotherapy molecules such as doxorubicin, for example, but PEG has never been proposed up until now to prevent or cure cancers.

The use of PEG according to the invention finds particular application in preventing the onset of colorectal cancers in persons genetically suffering from familial polyposis (FAP) or from Lynch's syndrome (HNPCC) and generally in persons over the age of 65 or who carry risk factors such as intestinal polyps, for example, and who could be given chronic preventive treatment.

This invention more particularly gives consideration to PEGs and their derivatives having a molecular weight of more than approximately 400, preferably more than approximately 1000, and further preferably having a high molecular weight in the order of approximately 3000 to 9000 daltons.

Polyethylenepolypropylene glycol, also known under the name "pluronic F68" or "poloxamer 188" and called "PLU" hereinafter, has a molecular weight of 8350. It is used as a food additive on account of its surfactant, lubricating and non-foaming properties. Pluronic F68 has the following formula (II):

$$HO(CH_2CH_2O)_{75}(CH(CH_3)CH_2OH)_{30}(CH_2CH_2O)_{75}H \quad (II)$$

PLU is marketed as a laxative medicine under the name Idrocol, and is an osmotic laxative which acts by increasing the water content of the feces and promoting their sliding movement along the intestine walls (Vidal 1997, p.814). PLU is also marketed as a medicinal product under the name Alkenide for protective or healing applications, in the form of a solution for local application and bathing, in particular for on-site cleansing and treating of skin and mucous membrane disorders (Vidal 1997, p. 48).

Under this invention, by "PLU" and "PEG" derivatives we mean the compounds of formulas I or II of which one or more reaction chemical groups are modified or substituted but which maintain their cancer prevention or curing ability. In particular, by "PLU derivative" we mean polyethylenepolypropylene glycols in which the chain link of the $CH_2CH_2O$ and $CH(CH_3)CH_2OH$ groups are different from those of formula II.

The invention particularly targets derivatives of PEG and PLU having hydrosoluble and lubricating properties in respect of the level of PEG and PLU in solution. Persons skilled in the art are able to test the prevention and curative capabilities of these PEG derivatives in colorectal cancers using the tests described in the experimental part set forth below.

Our work has revealed the remarkable colorectal cancer prevention properties of non-fermented osmotic laxatives compared with other types of laxatives. Among all the laxatives tested, PEG and PLU are the only effective ones. Laxatives that were tested which do not belong to this family had no preventive effect on colon carcinogenesis. On the contrary, karaya gum, which is a fermented bulking laxative, appears to have a rather more promoting effect. Paraffin oil, which is a non-fermented lubricating laxative, has no effect. As indicated above, the other fermented laxatives, such as bulking fibers (wheat bran, psyllium, etc.) or sugars which are fermented osmotic laxatives (lactulose and the like), have been studied at length and are thought to be slightly protective against colon carcinogenesis, but they never show the qualities of non-fermented osmotic laxatives identified under this invention.

The invention, therefore, also relates to a pharmaceutical composition containing as active ingredient polyethylene glycol or a derivative thereof, at least one non-fermented osmotic laxative associated in the composition with a pharmaceutically acceptable vehicle, for the prevention and treatment of colorectal cancers.

The invention particularly concerns PEG or PLU as an active ingredient or a derivative thereof or their mixtures.

As indicated above, the invention relates to compositions whose active ingredient is PEG and/or one of its derivatives having a molecular weight of more than approximately 400, preferably more than approximately 1000, and further preferably having a high molecular weight in the order of approximately 3000 to 9000 daltons.

Since the PEG is probably not absorbed, the invention particularly relates to any pharmaceutical composition in which the PEG or a derivative thereof is associated with a pharmaceutical vehicle in a form enabling administration by mouth, or in suppository form, or as a wash, or in any other form permitting action on the intestinal wall.

The dosage of the compositions of the invention is such that it provides for the administration of approximately 0.2 to 0.8 g/day of non-fermented osmotic laxative per kilogram of body weight or animal weight to be treated.

Therefore, the dosage of the pharmaceutical compositions of the invention is such that about 10 to about 80 g of non-fermented osmotic laxative can be taken per day. These values were determined using experimental results obtained in rats, on the basis of body surface ratios (equivalent to metabolic weight PO.72). Therefore, a daily dose of about 80 g PEG is considered appropriate for a person weighing approximately 100 kg. Extrapolating from rat to man may also be made on the basis of the intake of dry food weight per day. This method of calculation leads to an effective dose of non-fermented osmotic laxative of about 20 g per day for a person of average weight.

The above doses advantageously relate to oral administration of PEG and more particularly of PEG 8000.

All pharmaceutically acceptable vehicles that are compatible with the above modes of administration may be used in the pharmaceutical compositions of the invention.

The invention also concerns a functional food, also called a medicinal food or nutraceutic compound. This name denotes in particular a functional food, containing at least one non-fermented osmotic laxative, such as PEG or PLU, their derivatives or a mixture thereof, for use in the prevention of colon and/or rectum cancers. It is preferably PEG or a derivative thereof having a molecular weight of more than approximately 400, and preferably more than 1000, and further preferably having a high molecular weight, on the order of approximately 3000 to 9000 daltons, advantageously in the order of 8000 daltons.

The functional food has a twofold advantage, firstly, its role in the prevention of cancers of the rectum and/or colon in accordance with the invention, and secondly, a laxative effect according to the known properties of PEG. Therefore, the dose of a non-fermented osmotic laxative in the functional food promotes either the laxative effect at low doses of laxative, or the cancer prevention effect at higher doses as indicated above for the pharmaceutical compositions of the invention.

Other advantages and characteristics of the invention will become apparent on reading the following examples relating to the identification of PEG and PLU anti-cancer properties in rats.

I—EXAMPLE 1

Experiment with PEG

1) Material and Methods

This experiment, which allowed demonstration of the anti-cancer effect of PEG in rats, comprised 8 groups of 10 to 20 rats initiated with azoxymethane (AOM). In order to study the effect of stool hydration on carcinogenesis, some groups were given a salt diet (3 to 6% NaCl), others a liquid diet (water consumption 150 to 200% more than controls) or a diet with restricted water intake (90% of control intake) and, finally, a further group was treated with a diuretic (furosemide). The results given below only concern the control group and the group treated with PEG.

Fischer 344 rats, females aged 4 weeks (Iffa Credo, L'Arbresles 69) were kept for 5 days on their arrival, and were then given an intraperitoneal injection of azoxymethane (20 mg/kg live weight, in 9 g/l NaCl, Sigma, St Quentin 38). The rats were randomly divided 7 days later into cages, 2 rats per cage, using suspended metal cages with stainless steel bars, in an air-controlled animal room (22° C.±2° C.) with a day and night cycle of 12 h. The rats were then given ad libitum one of the protocol diets in porcelain, semicircular dishes that were renewed every week. Water was given in plastic drinking bottles, one bottle per cage.

Twenty control rats were given a semi-purified powder diet of standard composition (20% protein and 5% lipids, UAR, Villemoisson 91) (American Institute of Nutrition, 1977, report of the American Institute of Nutrition Ad Hoc Committee on standards for nutritional studies, J. Nutr. 107: 1340–1345), and ten treated rats were given the same diet to which PEG 8000 was added (ref. 194839 [25322-68-31__ from ICN, Orsay 91). The quantity of PEG was adjusted each week in relation to rat weight so that they were given 3 g/kg/day (approximately 5% dry food weight). The diets were given one week after the injection of the carcinogenic substance and for 100 days until the animals were sacrificed.

The rats were weighed before injection, and every week until they were sacrificed. The energy intake and the daily consumption of water and food of each rat were also recorded 1 day per week (on Tuesdays). After 100 days of experimental diet, the rats in each group were killed by $CO_2$ asphyxia, dissected, and the colon removed and emptied by injection of Krebs' Ringer buffer, opened and fixed flat between two sheets of filter paper (coded) in buffered formaldehyde (10%). After at least 12 h, the colons were stained with methylene blue (15 minutes, 0.2% in Krebs' Ringer). The microadenomas (aberrant crypt foci, ACF) were counted (number and size) under a microscope (×40) by a single observer for the entire experiment under double-blind conditions (Bird R. P., 1987, Cancer Lett. 37: 147–151 (Bruce W. R., Archer M. C., Corpet D. E., Medline A., Minkin S., Stamp D., Yin Y. and Zhang X. M., 1993, Mutation Research, 290: 111–118).

The following additional measurements were also made:
Transit rate: the transit time of a labeler for the solid phase of the digestive content, chromium, was measured.
Water content of the feces: the feces were weighed and counted 1 day/week (on Wednesdays), then the fresh and dry weight of these feces and, hence, the moisture content were determined.
Titration of fecal compounds: biliary acids, cytotoxicity of fecal water. These titration tests were conducted to test the hypothesis that protection against colon cancer is derived from dilution of the promoter or carcinogenic compounds in the fecal water.

Three supplemental studies were conducted. The purpose of the first study, H2, was to study the relationship between the dose of PEG and the protective effect. The second study, H4, was intended to demonstrate the short-term effect of PEG. The third study, H3, set out to show the effect of PEG on true intestinal cancers in the rat.

The relationship between PEG dose and the protective effect was studied in 42 Fischer 344 rats, males aged 4 weeks supplied by Iffa-Credo(Lyon). One week after their arrival, the rats were given a single injection of azoxymethane (20 mg/kg). They were divided at random into 4 batches and fed with a standard AIN76 powder diet containing 0; 0.5; 2 or 5% PEG. After 5 weeks of experimental diet, the rats were sacrificed, and the colons were prepared as described above.

The short-term effect of PEG was studied in 40 Fischer 344 rats, females divided at random into 4 batches. On arrival and for 16 days one of the batches of 10 rats was given an AIN75 diet containing 5% PEG (batch I). One week after their arrival all the rats were given a single injection of azoxymethane (20 mg/kg). One control batch was given a standard AIN76 powder diet and pure drinking water ad libitum (batch T). One week after the injection of azoxymethane, two experimental batches were given 5% PEG either in the food (batch A) or in the drinking water (batch E) for 30 days. After 30 days of experimental diet, the rats were sacrificed, and the colons were prepared as described above.

A third additional study, H3, was conducted to measure the effect of PEG on the onset of macroscopic tumors and cancers of the colon in the rat. Thirty F344 male rats, 7 days after an injection of carcinogenic azoxymethane (20 mg/kg), were given a food diet containing 20% cooked casein (2 h at 180° C.) and 20% lard. This food is a strong promoter of carcinogenesis in the rat (Corpet et al., Cancer research, 1990, 50: 6955). Ten rats chosen at random among the 30 were also given 5% PEG in this food. Euthanasia of the rats was carried out 88 days after the injection of the carcinogenic substance, and the number of tumors visible on each colon were counted and those with a surface area of more than 1 $mm^2$ were taken for conventional histological analysis after thin section (5 microns) and staining with Hemalun-Eosine.

2) Results

The results given in Tables 1, 2 and 3 below show extremely substantial inhibition by PEG of colon carcinogenesis, irrespective of the criterion chosen.

TABLE 1

Number of microadenomas per colon

| Group | Number of rats | Number of ACR/rat |
|---|---|---|
| Controls | 20 | 107 ± 43 |
| PEG | 10 | 6 ± 6 |
| P | | <0.0001 (Welch's test, unequal variances) |

TABLE 2

Multiplicity or number of crypts per microadenoma

| Group | Number of rats | Number of crypts/ACP |
|---|---|---|
| Controls | 20 | 2.9 ± 0.4 |
| PEG | 8 | 1.3 ± 0.4 |
| P | | <0.0001 (Student's test) |

TABLE 3

Incidence of large microadenomas with 3 or more crypts, and average number of large microadenomas per rat

| Group | Number of rats | Incidence | N° of large ACF |
|---|---|---|---|
| Controls | 20 | 20 (100%) | 58 ± 26 |
| PEG | 10 | 4 (40%) | 0.7 ± 1.2 |
| P | | 0.0004 (exact Fischer test) | 0.00001 (Mann-Whitney test) |

It is to be noted that two rats did not show any microadenoma. Therefore, Table 2 only takes into account the 8 rats which had at least one microadenoma.

The results that are not given in a table show that the rats treated with PEG showed similar growth to controls, ate as much food, and drank as much water as the controls. On the other hand, their fecal excretion was much higher:

Controls: 1.5+0.08
PEG treated: 3.46± 0.39 g/day
P<0.0001

Also, PEG greatly increased caecum weight (controls 2.1±0.4 compared with treated 6.6±0.9) and the water content of the feces (controls 12.6±2.4 compared with treated 38.6±5.0 and p<0.001).

The three supplemental studies H2, H3 and H4, whose methods are described above, largely confirmed the protective effect of PEG against colon carcinogenesis in the rat.

Study of the relationship between PEG dose and the protective effect enabled a very distinct relationship to be observed between the administered PEG dose and the protective effect.

In the groups of males rats who were given 0; 0.5; 2 or 5% PEG in their diet for 5 weeks, respectively 127±52, 110±45, 88±20 and 16±10 microadenomas were detected per colon (average of 14, 8, 10 and 10 rats, ± standard deviation). The global effect is very significant (ANOVA p<0.0001), but only the doses of 2 and 5% PEG significantly reduced the number of ACF. The multiplicity of ACF (mainly their size: precisely the number of aberrant crypts per ACF) was respectively 2.3; 2.2; 2.1; and 1.8 (pooled standard deviation of 0.2), the global effect being highly significant (p=0.0004), but only the dose of 5% had a significant effect compared with controls.

In respect of these two parameters for carcinogenesis, the relationship between PEG dose and the protective effect, is very distinct even if the dose of 5% is the only truly effective dose. Finally, this study shows that PEG is effective both in the males and in the females.

The short-term effect of PEG shows that the administration of 5% PEG for 30 days via the diet or drinking water, strongly reduces colon carcinogenesis, but less than over a longer time period, of 100 days for example.

On the other hand, PEG has no protective effect when it is administered during the tumor initiation period. The number of ACF per colon in the control animals (T) or in those who received PEG during the initiation period (16 days, I), or after initiation (30 days) either in the diet (A) or in the drinking water (E) was T: 65±31, I: 63±31, A: 8±8, E: 9±10 (average of 10 rats + standard deviation).

These results are highly significant (ANOVA p<0.0001), and groups A and E are similar and very different to the control group T (p<0.01) which is identical to group I. The differences between groups and levels of significance are similar in respect of ACF multiplicity: T: 2.0, I: 1.9, A: 1.6, E: 1.7 and in respect of the number of large ACF (more than 3 crypts/ACF): T: 5.6, I: 3.9, A: 0.3, E: 0.4. This study confirms the protective effect of PEG on chemically induced colon carcinogenesis in the rat.

In the H3 study on accelerated carcinogenesis, in rats given a very fatty diet containing cooked casein, PEG greatly reduced the number and incidence of tumors and cancers. Overall, 41 tumors were detected in the 20 control rats, compared with only 1 in the 10 who were given PEG. Tumor incidence was 14/20 in the controls compared with 1/10 in the "PEG" rats (p=0.005, exact Fischer test). The number of tumors per rat was 2.1 in the controls compared with 0.1 in the PEG rats (p=0.003), Mann-Whitney test). The results of histological analysis, verified by an anatomo-pathologist, show that the control rats had at least 15 adenocarcinomas (cancers) of which 6 were invasive, and 12 adenomas (non-malignant polyp). The only tumor detected in the rats given PEG was one adenoma. This H3 experiment leads to asserting that PEG protects rats against chemically induced colon cancer.

Globally, four independent studies conducted under varied conditions, by several experimenters (in particular for microadenoma reading) show the substantial protective effect of PEG on colon carcinogenesis. The observation of this protective effect cannot be due to chance.

In the following discussion, the protective property of PEG is compared with that of other molecules which are said to provide "chemoprevention" of colorectal carcinogenesis. PEG is by far the most effective product.

3) Discussion

Table 4 below shows the effectiveness of different agents on colon carcinogenesis in rats. This table gives a sample of 20 agents, including the 6 most effective among the 80 identified in the literature.

Each value is the ratio between the value in the controls given a carcinogenic substance and the value found in animals treated with a preventive agent before or after the carcinogenic substance. The higher the value the greater the effectiveness of the agent.

TABLE 4

| Agent | Ref | n° ACF/rat | Crypts/ACF | Large ACF |
|---|---|---|---|---|
| PEG | 1 | 18 | 2.28 | 104 |
| Perilla oil | 2 | 3.9 | 1.09 | |
| Inulin + bifid. longum | 7 | 3.7 | | 2.3 |
| Piroxicam | 8 | 2.8 | | 8 |
| DHA/PhIP | 9 | 2.8 | 1.13 | |
| Hesperidin 1000 ppp | 11 | 2.6 | 1.25 | |
| Auraptene 500 ppm | 11 | 2.3 | 1.33 | |
| 13 cis retinoic | 12 | 2.0 | | 1.9 |
| Dehydroepiandr. | 4 | 1.9 | 1.06 | |
| Oxothiazolidine | 4 | 1.9 | 1.09 | |
| Sulindac | 5 | 1.7 | 1.10 | |
| Aspirin | 12 | 1.7 | | 2.7 |
| Acetoxychavicol acet. | 11 | 1.7 | 1.13 | 2.1 |
| Piroxicam | 5 | 1.6 | 1.10 | |
| Fish oil K85 with AOM | 3 | 1.6 | | 1.8 |
| DHA/AOM | 10 | 1.6 | 1.08 | 2.0 |
| N-acetylcysteine | 4 | 1.5 | 1.10 | |
| Inulin 10% | 6 | 1.5 | | 1.4 |
| Vit. D3 | 8 | 1.3 | | 1.8 |
| Fish oil K85 wk17–23 | 3 | 1.2 | 1.08 | 1.6 |

The first column (n° ACF/rat) relates to the onset of microadenomas, the two other columns (crypt/ACF and Large ACF) are labelers of the growth of the microadenomas.

The first column (n° ACF/rat) relates to the onset of microadenomas, the two other columns (crypt/ACF and Large ACF) are labelers of the growth of the microadenomas.

The results given in Table 4 were established on the basis of published data indicated in references 2 to 12 in Table 5 below.

TABLE 5

| Publication | ACF/rat | Crypt/ACF | Large ACF |
|---|---|---|---|
| Control | 107 ± 43 | 2.9 ± 0.4 | 58 ± 26 |
| PEG | 6 ± 6 | 1.3 ± 0.4 | 0.7 ± 1.2 |
| Onogi et al. Carcinogenesis, 1996, 17, 1291–1296. | | | |
| Olive oil | 155 | 1.68 | |
| Perilla oil | 40 | 1.54 | |
| Paulsen et at. Pharmacol. & Toxicol., 1998, 82, 1291–1286 "Fish oil concentrate K85 enriched EPA & DHA 3 g/kg BW wk 0–6, 2xAOM wk 0 & 1" | | | |
| Control wk6 | 217 | | 26 |
| K85 3 mg with AOM wk 0–6 | 139 | | 14 |
| K85 1.5 mg post AOM wk 2–6 | 181 | | 25 |
| Control wk 23 | 96 | 5.2 | 11 |
| K85 2.2 mg post AOM wk 17–23 | 80 | 4.8 | 7 |
| Pereira-Khoury, Cancer Lett., 1991, 61:27–33 "Agent wk-1 to +4, 2x15 mg AOM at wk 0" | | | |
| Control | 228 ± 32 | 2.59 ± 0.14 | |
| N-acetylcysteine | 151 ± 21 | 2.35 ± 0.07 | |
| Dehydroepiandrosterone | 121 ± 19 | 2.44 ± 0.07 | |
| Oxothiazolidine | 121 ± 11 | 2.38 ± 0.08 | |
| Pereira et at., Carcinogenesis, 1994, 15:1049–1054, "Agent given for day 1–35, AOM on d. 7 & 14". | | | |
| Control | 26 ± 2.2 | 2.04 ± 0.04 | |
| Pyroxicam | 16 ± 2.8 | 1.84 ± 0.1 | |

TABLE 5-continued

| Publication | ACF/rat | Crypt/ACF | Large ACF |
|---|---|---|---|
| Sulindac | 15 ± 3.2 | 1.82 ± 0.14 | |
| Reddy et al., Carcinogenesis, 1997, 18:1371–1374, "Inulin or oligofruct for 10 wks, AOM at wk 3 & 4". | | | |
| Control | 120 | | 56 |
| Inulin 10% | 78 | | 39 |
| Rowland et al., Carcinogenesis, 1998, 19:281–285. "Bifid. & inulin x 12 wks, 7 d post AOM". | | | |
| Control | 130 | | 37 |
| Inulin + Bifid.longum | 35 | | 16 |
| Salim et al., Japanese Journal of Cancer Research, 88:1052–1062. "Vit. D3 postDMH for 16 wks". | | | |
| Control | 352 | | 120 |
| Vit. D3 10 ppm | 269 | | 66 |
| Takahashi et al. Carcino genesis 1997, 18:1937–1941. "ACF induced by 10x (PhIP) & DHA 4 h before each dose". | | | |
| Control | 22 | | 2.69 |
| DHA | 8 | | 2.39 |
| Takahashi et al. Carcinogenesis 1997, 18:1937–1941 (Correl. with adenocarcinoma) "ACF induced by 20x AOM & 1 ml DHA with each dose". | | | |
| Control 12w | 308 ± 64 | 3.2 | 114 |
| DHA 12w | 191 ± 40 | 2.95 | 56 |
| Tanaka et al., Carcinogenesis, 1997, 18:2155–2161. "(Correl./carcinoma) ACF induced by 3 x AOM 15 mg/kg". | | | |
| Control p. 957 | 89 ± 17 | 2.77 | |
| Hesperidin 1000 ppm | 34 ± 5 | 2.22 | |
| Control p. 1113 | 118 ± 28 | 2.54 | 60 |
| Acetoxychavicol acet 100 ppm | 70 ± 10 | 2.24 | 28 |
| Control p. 2155 | 157 ± 21 | 2.91 | |
| Auraptene | 69 ± 6 | 2.19 | |
| Wargovich et al. Int. J. Cancer 1995, 60:515–519. "AOM, then 4 wks, then agent given for 4 wks". | | | |
| Control/asp | 175 | | 55 |
| Aspirin 0.2 g/kg | 100 | | 20 |
| Control/pir | 125 | | 40 |
| Piroxicam 0.2 | 45 | | 5 |
| Control/ret | 140 | | 57 |
| 13 cis Retinoic | 70 | | 30 |

The results recorded in Table 4 show that PEG is the most effective agent in the prevention of chemically induced colorectal carcinogenesis in the rat. Table 4 enables a comparison between the effectiveness of PEG and that of other agents. Moreover, most of the agents given in Table 4 were administered before and during initiation of the tumors. They could, therefore, have acted simply by blocking the carcinogenic substance or by inhibiting its metabolism.

As it is highly improbable that colorectal cancers in man are initiated by azoxymethane, this greatly limits the interest of these agents. PEG, on the other hand, was administered one week after the injection of the carcinogenic azoxymethane.

PEG, therefore, had a curative effect on the microadenomas and cancers, independently from the carcinogenic substance which is metabolized and excreted in less than 24 hours.

4) Effect of PEGs with Different Molecular Weights

Method

A group of 32 F344 rats was given an injection of carcinogenic azoxymethane (20 mg/kg), and 7 days later was divided into a control group of 12 rats and 5 experimental groups of 4 rats. The experimental groups were given, in their drinking water, 5% PEG having a molecular weight of between 400 and 20 000. PEG 8000 was given to two groups at doses of 5 or 10%.

Results

The results are given in Table 6 below. It would appear that PEG 8000 at a 5% dose is more effective in suppressing ACF. Table 6 shows that the number of ACF per rat, or the number of large ACF per rat, follows a U-shaped curve in relation to the molecular weight of ingested PEG. The lower point of this U-curve relates to the group which was given 5% PEG 8000. However, the difference between the 3350 and 8000 PEGs is not significant, no doubt owing to the low number of rats per group.

As in the experiment described in Example 2 below, there is no correlation between the laxative effect of the products, measured by the water percentage of stools, or the weight of stools excreted in 24 hours, or caecum weight, and carcinogenesis data (number of ACF, ACF size, number of large ACF).

TABLE 6

| PEG | | | Large ACF 4 | water % in stools | | |
|---|---|---|---|---|---|---|
| M.W. | Dose | N° ACF | or over | 24 h | Fresh | Weight of feces |
| Control | 0% | 135 | 18.7 | 11.8 | 28 | 1.4 |
| 400 | 5% | 97.5 | 5.2* | 48.3* | 74* | 2.8* |
| 3350 | 5% | 46.5* | 5.7* | 31.7* | 66* | 2.6* |
| 8000 | 5% | 23.3* | 1.2* | 35.6* | 67* | 3.0* |
| 8000 | 10% | 43.3* | 3.0* | 147.0* | 66* | 4.5* |
| 20000 | 5% | 64.8* | 6.2* | 129.7* | 67* | 4.2* |

*: very significant difference with control, p < 0.01
II -Example 2: Experiments with PLU and PEG

II—EXAMPLE 2

Experiments with PLU and PEG

1) Material and Methods

The experiment consisted of giving 44 F344 rats, males aged 5 weeks, an injection of carcinogenic azoxymethane (20 mg/kg), then dividing the group 7 days later into different batches which were given a powder diet based on the AIN 76 formula, containing 5% PEG or PLU or other substances shown in Table 7 below.

TABLE 7

| Test | Composition | RATS |
|---|---|---|
| Control | AIN 76 powder | 12 |
| PLU | AIN 76 powder with 5% Pluronic F 68 | 4 |
| PEG | AIN 76 powder with 5% PEG 8000 ICN | 4 |
| CAR | AIN 76 powder with 5% carboxymethylcellulose | 4 |
| PVP | AIN 76 powder with 5% polivinylpyrrolidone | 4 |
| PFA | AIN 76 powder with 5% PEG fatty alcohol ether | 4 |
| POE | AIN 76 powder with 5% polyoxyethylene fatty acids | 4 |

TABLE 7-continued

| Test | Composition | RATS |
|---|---|---|
| | esters | |
| KAR | AIN 76 powder with 5% Karaya gum | 4 |
| HUI | AIN 76 powder with 5% paraffin oil | 4 |

2) Results and Discussion

The results and discussion below only concern PEG and PLU, since the other products tested did not show any protective effect or, on the contrary, showed a promoting effect on the growth of microadenomas (ACF).

The highly protective effect of PEG can be seen as in Example 1: all $p<0.001$, with fewer ACF: 3.72 compared with 52.8 in 11 controls, and fewer large ACF: 2.5 compared with 39 (2 or more), 1.25 compared with 17 (3 or more), 0.5 compared with 6.8 (4 or more).

In respect of PLU, a more protective effect is observed than with PEG: all $p<0.001$, fewer ACF than controls: 0.75 compared with 52.8, and much fewer large ACF: 0.25 compared with 39 (2 or more), 0.25 compared with 17 (3 or more), 0.0 compared with 6.8 (4 or more).

It appears that PLU is more effective than PEG. However, it is difficult to compare the results obtained with 4 PLU rats and 4 PEG rats, since the differences are not sufficiently significant:

Number of ACF: 10.75 against 3.75

Number of large ACF: 2 or more: 0.25 against 2.5 $p=0.23$; 4 or more: 0.0 against 0.5.

Multiplicity: 1.5 against 2.22, but there are only two rats with ACF per group.

Moreover, PLU could offer the advantage of being less laxative than PEG in man. Indeed, in the rat PEG increases caecum weight by 120%, while PLU only causes an increase of 40% (TEM 3.3 g, PEG 7.3 g, PLU 4.8 g, all $p<0.001$). On the other hand, fecal excretion is largely increased compared with controls and similar in the PEG and PLU groups (TEM 1.9 g/day, PEG 4.8 g, PLU 5.6 g), similarly the water content of stools (TEM 30%, PEG 68%, PLU 64%). Finally, neither PLU nor PEG altered the weight gain in treated rats compared with controls (TEM 269.9 g, PEG 270.1 g, PLU 267.7 g).

What is claimed is:

1. A method of treating colon or rectum cancer comprising administering to a mammal a therapeutically effective amount of a non-fermented osmotic polyol laxative.

2. The method of claim 1, wherein the non-fermented osmotic laxative is polyethylene glycol or polyethylenepolypropylene glycol, a mixture or a derivative thereof.

3. The method of claim 2, wherein the polyethylene glycol or the derivative thereof has a molecular weight of more than approximately 400, and has a high molecular weight of about 3000 to about 9000 daltons.

4. The method of claim 2, wherein the polyethylene glycol or the derivative thereof has a molecular weight of more than approximately 1000, and has a high molecular weight of about 3000 to about 9000 daltons.

5. The method of claim 2, wherein the polyethylene glycol or the derivative thereof has a molecular weight of more than approximately 400, and has a high molecular weight of about 8000 daltons.

6. A method of preventing colon or rectum cancer comprising administering to a mammal a therapeutically effective amount of a non-fermented osmotic polyol laxative.

7. The method of claim 6, wherein the non-fermented osmotic laxative is polyethylene glycol or polyethylenepolypropylene glycol, a mixture or a derivative thereof.

8. The method of claim 7, wherein the polyethylene glycol or the derivative thereof has a molecular weight of more than approximately 400, and has a high molecular weight of about 3000 to about 9000 daltons.

9. The method of claim 7, wherein the polyethylene glycol or the derivative thereof has a molecular weight of more than approximately 1000, and has a high molecular weight of about 3000 to about 9000 daltons.

10. The method of claim 7, wherein the polyethylene glycol or the derivative thereof has a molecular weight of more than approximately 400, and has a high molecular weight of about 8000 daltons.

11. The method of claim 1, wherein said mammal is selected from the group consisting of persons genetically suffering from familial polyposis or Lynch's syndrome, elderly persons and persons carrying risk factors.

12. The method of claim 6, wherein said mammal is selected from the group consisting of persons genetically suffering from familial polyposis or Lynch's syndrome, elderly persons carrying risk factors.

* * * * *